US012745972B2

(12) United States Patent
Zhu et al.

(10) Patent No.: US 12,745,972 B2
(45) Date of Patent: Sep. 29, 2026

(54) X-RAY IMAGING SYSTEM AND X-RAY IMAGING METHOD FOR DYNAMIC EXAMINATION

(71) Applicant: GE Precision Healthcare LLC, Waukesha, WI (US)

(72) Inventors: Chao Zhu, Beijing (CN); Hongjiang Li, Beijing (CN); Qiong Li, Beijing (CN); Lin Lin, Beijing (CN); Yan Wang, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 272 days.

(21) Appl. No.: 18/532,241

(22) Filed: Dec. 7, 2023

(65) Prior Publication Data

US 2024/0188920 A1 Jun. 13, 2024

(30) Foreign Application Priority Data

Dec. 12, 2022 (CN) ......................... 202211589561.0

(51) Int. Cl.
*A61B 6/00* (2024.01)
*G06T 7/73* (2017.01)

(52) U.S. Cl.
CPC .............. *A61B 6/545* (2013.01); *A61B 6/488* (2013.01); *A61B 6/542* (2013.01); *G06T 7/73* (2017.01);

(Continued)

(58) Field of Classification Search
CPC .. A61B 6/542; A61B 6/08; A61B 6/00; A61B 6/488; A61B 6/544; A61B 6/545; A61B 6/5294; A61B 6/5235; A61B 34/20; A61B 6/583; A61B 6/4441; A61B 6/5205; A61B 6/52; A61B 6/4405; A61B 6/5223; A61B 6/582; A61B 6/032; A61B 6/12; A61B 6/584; A61B 2090/376;

(Continued)

(56) References Cited

U.S. PATENT DOCUMENTS 11,701,075 B2 * 7/2023 Vancamberg ........ A61B 6/5235 378/177
2012/0219119 A1 * 8/2012 Arima .................... A61B 6/461 378/165

(Continued)

*Primary Examiner* — Irakli Kiknadze

(57) ABSTRACT

The present application provides an X-ray imaging system and an X-ray imaging method for dynamic examination. The X-ray imaging system comprises: a first camera and a control apparatus; the first camera being used to acquire a first optical image of an object under examination, and the control apparatus comprising a protocol selection unit, a pose determination unit and an exposure control unit; the protocol selection unit is used to select a corresponding protocol based on information of the object under examination, the protocol at least comprising a preset pose for exposure and an exposure site; the pose determination unit is used to identify key points on the first optical image, and to determine, based on the key points, whether the pose of the object under examination satisfies the preset pose; and the exposure control unit is configured to control exposure when the preset pose is satisfied and the location of the exposure site of the object under examination is within an exposure range, so as to acquire an X-ray image corresponding to the preset pose.

13 Claims, 9 Drawing Sheets

(52) U.S. Cl.
CPC ............... *G06T 2207/10116* (2013.01); *G06T 2207/10144* (2013.01)

(58) Field of Classification Search
CPC .... A61B 2034/2065; A61B 2034/2055; A61B 2090/367; A61B 2090/3966; A61B 6/469; A61B 6/4208; A61B 6/461; A61B 6/505; A61B 6/463; A61B 6/588; A61B 6/547; A61B 6/54; A61B 6/5241; A61B 6/5211; A61B 6/4452; A61B 6/4464; A61B 6/465; A61B 6/482; A61B 6/0407; A61B 6/04; A61B 6/40; A61B 6/4014; A61B 6/467; A61B 6/589; G06T 7/73; G06T 2207/10144; G06T 2207/10116; G06T 11/006; G06T 19/20; G06T 15/08; G06T 7/33; G06T 2211/436; G06T 2210/41; G06T 2207/20084; G06T 2211/441; G06T 2207/30204; G06T 2207/10081; G06T 2219/2004; G06T 7/0012; G06T 2207/30012; G06T 1/20; G06T 2207/30008; G06T 3/00; G06T 2207/10024; G06T 2207/20081; G06T 7/11; G06T 7/20; G06T 7/70; G06T 11/00; G06T 7/0016; G06T 2207/30168; G06T 2207/30196; G06T 2207/20132; G06T 2207/30004; G06N 3/045; G06N 3/08; G06N 3/084; G06N 3/09; G06N 3/0464; G06N 20/00; G06N 3/0895; G06N 3/063; G06N 3/048; G06N 3/044; G03B 17/561; H04N 19/543; H04N 19/573; G06V 40/10; G06V 40/11; G06V 40/23; G06V 20/46; G06V 2201/07; G06V 10/82; G06V 10/751; G06V 20/653; G06V 20/20; G06V 10/454; G06V 20/64; G06F 18/2148; B25J 9/161; B25J 19/023; B25J 9/1697; B25J 13/08; B25J 9/1612; B25J 9/163; B25J 9/1635; B25J 9/1664; G05B 13/027; G05B 2219/31305; G05B 2219/39311
USPC ................................................. 378/4, 62, 63
See application file for complete search history.

(56) References Cited

U.S. PATENT DOCUMENTS

2016/0029991 A1* 2/2016 Tajima ................... A61B 6/467 250/336.1
2023/0016072 A1* 1/2023 Sugahara ............... A61B 6/461
2023/0148978 A1* 5/2023 Zheng ..................... G06F 18/24 378/62
2023/0267608 A1* 8/2023 Horiuchi .............. G03B 17/561 348/61
2024/0081765 A1* 3/2024 Kitano ..................... A61B 6/54
2024/0415476 A1* 12/2024 Sugahara .................. G06T 7/11

* cited by examiner

400

X-RAY IMAGING SYSTEM AND X-RAY IMAGING METHOD FOR DYNAMIC EXAMINATION

CROSS REFERENCE TO RELATED APPLICATIONS

The present application claims priority and benefit of Chinese Patent Application No. 202211589561.0 filed on Dec. 12, 2022, which is incorporated herein by reference in its entirety.

TECHNICAL FIELD

The present invention relates to medical imaging technology, and specifically relates to an X-ray imaging system and an X-ray imaging method for dynamic examination.

BACKGROUND

In an X-ray imaging system, radiation from an X-ray source is emitted toward a subject, and the object under examination is usually a patient in a medical diagnosis application. A part of the radiation passes through the object under examination and impacts a detector, which is divided into a matrix of discrete elements (e.g., pixels). The detector elements are read to generate an output signal on the basis of the amount or intensity of radiation that impacts each pixel region. The signal can then be processed to generate a medical image that can be displayed for review, and the medical image can be displayed in a display apparatus of the X-ray imaging system.

Typically, for an object under examination, only a static X-ray image, e.g., a chest radiograph, needs to be captured to see a lesion in a pair of lungs. However, for some bone and joint sites that need to be captured, such as the neck, knee and shoulder, an image of the joint in a dynamic state needs to be captured, so as to perform dynamic examination of the joint and other sites. However, in the actual image capture process, the movement of the joint and the magnitude of the movement are difficult for the object under examination, and monitoring or guidance of the magnitude and location of the movement of the object under examination is difficult for an operator.

SUMMARY

The present invention provides an X-ray imaging system and an X-ray imaging method for dynamic examination.

Exemplary embodiments of the present invention provide an X-ray imaging system. The X-ray imaging system comprises: a first camera and a control apparatus; the first camera is used to acquire a first optical image of an object under examination, and the control apparatus comprises a protocol selection unit, a pose determination unit and an exposure control unit; the protocol selection unit is used to select a corresponding protocol based on information of the object under examination, the protocol at least comprising a preset pose and an exposure site; the pose determination unit is used to identify key points on a first optical image, and to determine, based on the key points, whether the pose of the object under examination satisfies the preset pose; and the exposure control unit is used to control exposure when the preset pose is satisfied and the location of the exposure site of the object under examination is within an exposure range, so as to acquire an X-ray image corresponding to the preset pose.

Exemplary embodiments of the present invention provide an X-ray imaging system. The X-ray imaging system comprises a first camera, a second camera, a control apparatus, and a display, the first camera and the second camera being used to acquire a first optical image and a second optical image of an object under examination, respectively, the control apparatus being configured to identify key points on the second optical image, the display comprising a graphical user interface configured to display a configuration interface, the first optical image and the second optical image, the configuration interface comprising at least one among information of the object under examination, an exposure protocol, and a 'ready to expose' prompt, at least one among the location of an exposure site and an exposure range being displayed on the first optical image, the key points being displayed on the second optical image, and the 'ready to expose' prompt being displayed when the key points on the second optical image satisfy a preset pose and the location of the exposure site in the first optical image is within the exposure range.

Exemplary embodiments of the present invention further provide an X-ray imaging method for dynamic examination, the method comprising: acquiring information of an object under examination; selecting a corresponding protocol based on the information of the object under examination, the protocol at least comprising a first pose and a second pose for exposure, and an exposure site; acquiring an optical image and identifying key points in the optical image, and determining, based on the key points, whether the pose of the object under examination satisfies the first pose or the second pose; and controlling exposure when the first pose or the second pose is satisfied and the location of the exposure site of the object under examination is within an exposure range, so as to acquire a first X-ray image corresponding to the first pose and a second X-ray image corresponding to the second pose, respectively.

Exemplary embodiments of the present invention further provide an X-ray imaging method for dynamic examination, the method comprising: acquiring information of an object under examination; selecting a corresponding protocol based on the information of the object under examination, the protocol at least comprising a preset pose for exposure and an exposure site; acquiring a first optical image, and generating a first control instruction when the pose of the object under examination in the first optical image satisfies the preset pose; acquiring a second optical image, and generating a second control instruction when the location of the exposure site of the object under examination in the second optical image is within an exposure range; and based on the first control instruction and the second control instruction, controlling exposure to acquire an X-ray image corresponding to the preset pose.

Other features and aspects will become apparent from the following detailed description, drawings, and claims.

BRIEF DESCRIPTION OF THE DRAWINGS

The present invention can be better understood by means of the description of the exemplary embodiments of the present invention in conjunction with the drawings, in which.

DETAILED DESCRIPTION

Specific embodiments of the present invention will be described below. It should be noted that in the specific description of said embodiments, for the sake of brevity and conciseness, the present description cannot describe all of the features of the actual embodiments in detail. It should be understood that in the actual implementation process of any embodiment, just as in the process of any one engineering project or design project, a variety of specific decisions are often made to achieve specific goals of the developer and to meet system-related or business-related constraints, which may also vary from one embodiment to another. Furthermore, it should also be understood that although efforts made in such development processes may be complex and tedious, for a person of ordinary skill in the art related to the content disclosed in the present invention, some design, manufacture, or production changes made on the basis of the technical content disclosed in the present disclosure are only common technical means, and should not be construed as the content of the present disclosure being insufficient.

Unless defined otherwise, technical terms or scientific terms used in the claims and description should have the usual meanings that are understood by those of ordinary skill in the technical field to which the present invention belongs. The terms "first" and "second" and similar terms used in the description and claims of the patent application of the present invention do not denote any order, quantity, or importance, but are merely intended to distinguish between different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections.

Figure 1:
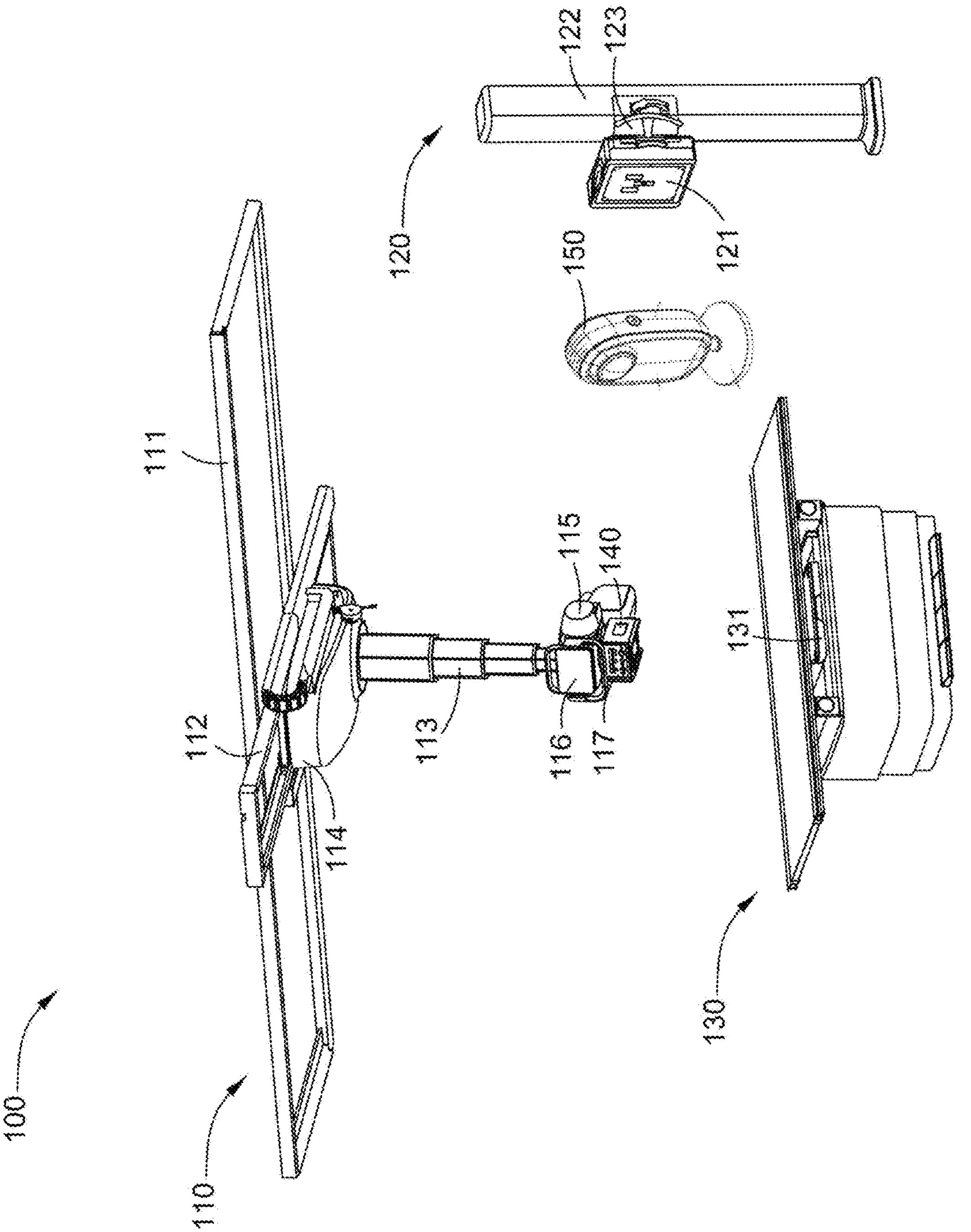
FIG. 1 is a schematic diagram of an X-ray imaging system according to some embodiments of the present invention.

FIG. 1 shows an X-ray imaging system 100 according to some embodiments of the present invention. As shown in FIG. 1, the X-ray imaging system 100 includes a suspension apparatus 110, a wall stand apparatus 120, and an examination table apparatus 130. The suspension apparatus 110 includes a longitudinal guide rail 111, a transverse guide rail 112, a telescopic cylinder 113, a sliding member 114 and a tube assembly 115.

For ease of description, in the present invention, the x-axis, y-axis, and z-axis are defined as the x-axis and y-axis being located in the horizontal plane and perpendicular to one another, and z-axis being perpendicular to the horizontal plane. Specifically, the direction in which the longitudinal guide rail 111 is located is defined as the x-axis, the direction in which the transverse guide rail 112 is located is defined as the y-axis direction, and the direction of extension of the telescopic cylinder 113 is defined as the z-axis direction, and the z-axis direction is the vertical direction.

The longitudinal guide rail 111 and the transverse guide rail 112 are perpendicularly arranged, the longitudinal guide rail 111 being mounted on a ceiling and the transverse guide rail 112 being mounted on the longitudinal guide rail 111. The telescopic cylinder 113 is configured to carry the tube assembly 115.

The sliding member 114 is provided between the transverse guide rail 112 and the telescopic cylinder 113. The sliding member 114 may include components such as a rotating shaft, a motor, and a reel, etc. The motor can drive the reel to rotate around the rotating shaft, which in turn drives the telescopic cylinder 113 to move along the z-axis and/or slide relative to the transverse guide rail. The sliding member 114 is capable of sliding relative to the transverse guide rail 112, i.e., the sliding member 114 is capable of driving the telescopic cylinder 113 and/or the tube assembly 115 to move in the y-axis direction. Further, the transverse guide rail 112 can slide relative to the longitudinal guide rail 111, which in turn drives the telescopic cylinder 113 and/or the tube assembly 115 to move in the x-axis direction.

The telescopic cylinder 113 includes a plurality of cylinders having different inner diameters, and the plurality of cylinders can be sleeved, sequentially from bottom to top, in the cylinder located thereabove, thereby achieving telescoping, and the telescopic cylinder 113 can be telescopic (or movable) in the vertical direction, i.e., the telescopic cylinder 113 can drive the tube assembly to move along the z-axis direction. The lower end of the telescopic cylinder 113 is further provided with a rotating part, and the rotating part can drive the tube assembly 115 to rotate.

The tube assembly 115 includes an X-ray tube, and the X-ray tube may produce X-rays and project the X-rays to an intended region of interest (ROI) of a patient. Specifically, the X-ray tube may be positioned adjacent to a beam limiter, the beam limiter being used to align the X-rays with the intended region of interest of the patient. At least a portion of the X-rays may be attenuated by means of the patient, and may be incident on a detector 121/131.

The suspension apparatus 110 further includes a beam limiter 117, which is usually mounted below the X-ray tube, and the X-rays emitted by the X-ray tube irradiate on the body of an object under examination by means of an opening of the beam limiter 117. An irradiation range of the X-rays, namely the region size of an exposure field of view (FOV), depends on the size of the opening of the beam limiter 117. The locations of the X-ray tube and beam limiter 117 in the transverse direction determine the location of the exposure FOV on the object under examination's body. It is well known that X-rays are harmful to the human body, so it is necessary to control the X-rays so that the X-rays only irradiate the site of the object under examination that needs to be examined, namely, the region of interest (ROI).

The suspension apparatus 110 further includes a tube console 116, the tube console 116 being mounted on the tube assembly. The tube console 116 includes user interfaces such as a display screen and a control button, used to perform preparation work before image capture, such as patient selection, protocol selection, positioning, etc.

The movement of the suspension apparatus 110 includes the movement of the tube assembly along the x-axis, y-axis, and z-axis, as well as the rotation of the tube assembly in the horizontal plane (the axis of rotation is parallel to or overlaps with the z-axis) and in the vertical plane (the axis of rotation is parallel to the y-axis). In the above motion, a motor is usually used to drive a rotating shaft which in turn drives corresponding components to rotate in order to achieve the corresponding movement or rotation, and the corresponding control components are generally mounted in the sliding member 114. An X-ray imaging unit further includes a motion control unit (not shown in the figure), and the motion control unit can control the described motion of the suspension apparatus 110. Furthermore, the motion control unit can receive a control signal to control a corresponding component to move correspondingly.

The wall stand apparatus 120 includes a first detector assembly 121, a wall stand 122, and a connecting portion 123. The connecting portion 123 includes a support arm that is vertically connected in the height direction of the wall stand 122 and a rotating bracket that is mounted on the support arm, and the first detector assembly 121 is mounted on the rotating bracket. The wall stand apparatus 120 further includes a detector driving apparatus that is arranged between the rotating bracket and the first detector assembly 121, which is driven by the detector driving apparatus to move in a direction parallel to the height direction of the wall stand 122 in the plane held by the rotating bracket, and the first detector assembly 121 can further be rotated relative to the support arm to form an angle with the wall stand. The first detector assembly 121 has a plate-like structure, the orientation of which is variable, facilitating an X-ray incident surface to become vertical or horizontal depending on the incident direction of the X-rays.

A second detector assembly 131 is included on an examination table apparatus 130, and the selection or use of the first detector assembly 121 and the second detector assembly 131 may be determined on the basis of an image capture site of a patient and/or an image capture protocol, or may be determined on the basis of the location of the object under examination that is obtained by image capture by a camera, so as to perform image capture and examination in a lying or standing position. FIG. 1 only shows an example diagram of a wall stand and an examination table, and it should be understood by those skilled in the art that wall stands and/or examination tables of any form or arrangement can be selected, or only the wall stand can be mounted, and the wall stand and/or examination table is not intended to limit the overall solution of the present application.

In some embodiments, the X-ray imaging system further includes a first camera configured to acquire a first optical image of the object under examination. The first optical image can be used to acquire the pose of the object under examination, and furthermore, the first optical image can further be used to acquire at least one among the thickness, the height, the location and the position of the object under examination.

In some embodiments, the X-ray imaging system further includes a second camera used to acquire a second optical image of the object under examination, so as to acquire at least one among the thickness, the height, the location, and the distance to a detector surface of the object under examination.

Specifically, one among the first camera and the second camera is mounted on the ground at a side of the wall stand apparatus 120 or inside of a scan room, and the other among the first camera and the second camera is mounted on the suspension apparatus.

In some embodiments, the first camera 140 is mounted on the ground at a side of the wall stand apparatus 120, and the second camera 150 is mounted on the suspension apparatus, for example, mounted at a side of the beam limiter 117, or the first camera is mounted at a side of the beam limiter, and the second camera is mounted on the ground at a side of the wall stand apparatus.

In some other embodiments, the first camera is mounted on the beam limiter, and the second camera is mounted inside of the scan room at a fixed location, e.g., on a wall of the scan room, or the first camera is mounted on a wall inside of the scan room, and the second camera is mounted on the beam limiter.

In yet some other embodiments, the X-ray imaging system further includes a third camera. The third camera is mounted inside of the scan room at a fixed location, while one among the first camera and the second camera is mounted on the ground at a side of the wall stand apparatus, and the other among the first camera and the second camera is mounted on the suspension apparatus, and preferably, at a side of the beam limiter.

The first camera and the second camera may include one or more capture devices, for example, a digital camera, an analog camera, etc., or a depth camera, an infrared camera, or an ultraviolet camera, etc., or a 3D camera, a 3D scanner, etc., or a red, green, and blue (RGB) sensor, an RGB depth (RGB-D) sensor, or other devices that can capture color image data of a target object. The first camera and the second camera may acquire depth information or a depth image of the object under examination, and the depth information may be used to determine the coordinate location of the center of the region of interest of the object under examination.

In some embodiments, the optical images acquired by the first camera and the second camera are not limited to a single optical image, but may also include a dynamic real-time video, i.e., a series of real-time optical pictures.

In some embodiments, the mounting location and angle of the camera mounted at a side of the wall stand apparatus depend on the location and angle in which a full-body optical photograph of the object under examination can be acquired. Specifically, the camera is mounted at a location having a preset height, e.g., a height of 1 meter above the ground, and the camera is mounted at a preset distance from the wall stand apparatus, such that the preset distance can enable the camera to acquire a full-body photograph of the object under examination.

In some embodiments, the first camera and the second camera are perpendicularly arranged. Specifically, image capture ranges of the first camera and the second camera are perpendicular to each other, and one among the first camera and the second camera is used to acquire a front photograph of the object under examination, and the other among the first camera and the second camera is used to acquire a side photograph of the object under examination. Specifically, when the object under examination is captured at a front or back position, that is, when the object under examination faces toward or away from the first detector assembly of the wall stand apparatus, the camera mounted on the suspension apparatus can acquire a front or back photograph of the object under examination, and the camera mounted at a side of the wall stand apparatus can acquire a side photograph of the object under examination. Likewise, when the object under examination is captured at a left or right side position, that is, when the object under examination is facing sideways relative to the first detector assembly of the wall stand apparatus, the camera mounted on the suspension apparatus can acquire a side photograph of the object under examination, and the camera mounted at a side of the wall stand apparatus can acquire a front or back photograph of the object under examination.

Generally, the depth information is obtained by means of a calculation from a 3D point cloud acquired by a camera. However, said depth information is the depth of one side of the object under examination from a detector surface, and when the object under examination is relatively far from the detector surface, the depth information is not precise. Therefore, in the present application, by acquiring the pose of the object under examination by means of one camera and acquiring the depth information of the object under examination by means of the other camera, precise depth information can be acquired, and the depth information can be used to determine exposure voltage and current.

The X-ray imaging system further includes a control apparatus (not shown in the figures), which may be a main control apparatus that is located in a control room, a tube console that is mounted on the suspension apparatus, a mobile or portable control apparatus, or any combination of the above. The control apparatus may include a source control apparatus and a detector control apparatus. The source control apparatus is used to command the X-ray source to emit X-rays for image exposure. The detector control apparatus is used to select a suitable detector among a plurality of detectors, and to coordinate the control of various detector functions, such as automatically selecting a corresponding detector according to the location or pose of the object under examination. Alternatively, the detector control apparatus may perform various signal processing and filtering functions, specifically, for initial adjustment of a dynamic range, interleaving of digital image data, and the like. In some embodiments, the control apparatus may provide power and timing signals for controlling the operation of the X-ray source and the detector.

In some embodiments, the control apparatus may also be configured to use a digitized signal to reconstruct one or more required images and/or determine useful diagnostic information corresponding to a patient, and the control apparatus may include one or more dedicated processors, graphics processing units, digital signal processors, microcomputers, microcontrollers, application-specific integrated circuits (ASICs), field-programmable gate arrays (FPGAs), or other appropriate processing apparatuses.

Of course, the X-ray imaging system may also include other numbers, configurations or forms of control apparatuses, for example, the control apparatus may be local (e.g., co-located with one or more X-ray imaging systems 100, such as within the same facility and/or the same local network); in other implementations, the control apparatus may be remote, and thus accessible only by means of a remote connection (e.g., by means of the Internet or other available remote access technologies). In a specific implementation, the control apparatus may also be configured in a cloud-like means, and may be accessed and/or used in a means that is substantially similar to the means by which other cloud-based systems are accessed and used.

The X-ray imaging system 100 also includes a storage apparatus (not shown in the figures). The control apparatus may store the digitized signal in the storage apparatus. For example, the storage apparatus may include a hard disk drive, a floppy disk drive, a CD-read/write (CD-R/W) drive, a digital versatile disc (DVD) drive, a flash drive, and/or a solid-state storage apparatus. The storage apparatus is used to store a program that can be executed by a computer. Of course, the storage apparatus may also be integrated with the control apparatus, so as to effectively use the footprint and/or meet expected imaging requirements.

In one embodiment, the X-ray imaging system 100 further includes an operator workstation, the operator workstation allowing the user to receive and evaluate the reconstructed image, and input a control instruction (an operation signal or a control signal). The operator workstation may include a user interface (or user input device) in a certain form of operator interface, such as a keyboard, a mouse, a voice activated control apparatus, or any other suitable input device, such that an operator may input an operation signal/control signal to the control apparatus by means of the user interface.

Figure 2:
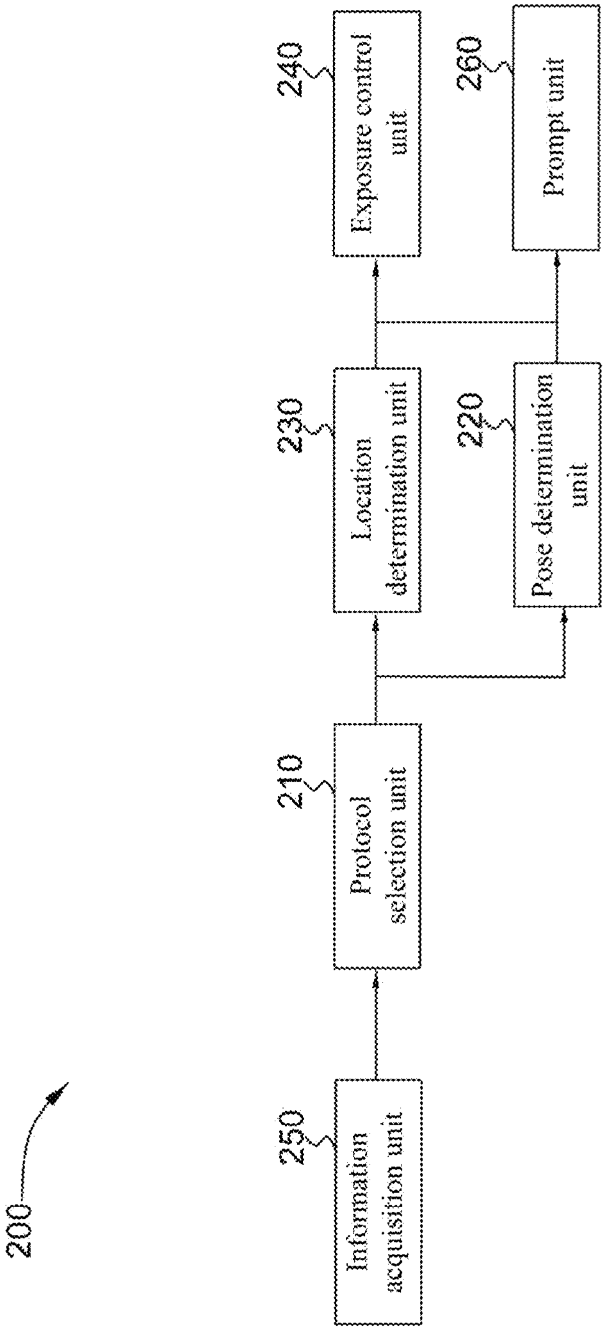
FIG. 2 is a schematic diagram of a control apparatus in an X-ray imaging system according to some embodiments of the present invention.

FIG. 2 shows a schematic diagram of a control apparatus in an X-ray imaging system. As shown in FIG. 2, the control apparatus 200 includes a protocol selection unit 210, a pose determination unit 220, and an exposure control unit 240. Specifically, the protocol selection unit 210 is used to select a corresponding protocol based on information of the object under examination, the protocol at least including a preset pose for exposure and an exposure site. The pose determination unit 220 is used to identify key points on a first optical image, and determine, based on the key points, whether the pose of the object under examination satisfies the preset pose. The exposure control unit 240 is used to control exposure when the pose of the object under examination satisfies the preset pose and the location of the exposure site is within an exposure range, so as to acquire an X-ray image corresponding to the preset pose.

In some embodiments, the control apparatus 200 further includes a location determination unit 230, the location determination unit 230 being used to determine whether the location of the exposure site of the object under examination is within the exposure range.

In some embodiments, the control apparatus further includes an information acquisition unit 250. The information acquisition unit 250 is configured to acquire the information of the object under examination. In some other embodiments, at least one among the first camera and the second camera is used to acquire the information of the object under examination. Specifically, the information of the object under examination is acquired by scanning at least one among a barcode, a two-dimensional code, an identity card, a radio frequency tag (RFID), and a medical card of the object under examination.

In some embodiments, the information of the object under examination can be acquired by scanning an identity code corresponding to the object under examination, for example, by scanning a two-dimensional code, barcode, identity card, radio frequency tag, medical card, etc., of the patient. The information can be acquired by means of the first camera or the second camera, or may be acquired by means of an external card reading device. In some non-limiting embodiments, when entering a device room or the scan room, the patient may align the identity code carried by the patient with the camera at a side of the wall stand apparatus, and the camera can acquire an optical image that has the identity code, and identify the identity information of the patient based on the image.

Specifically, the information of the object under examination includes at least one among a name, age, exposure site, possible type of disease, type of image capture, etc.

The protocol selection unit 210 can automatically select a corresponding image capture protocol based on the identity information of the object under examination. Specifically, the protocol includes a preset pose for exposure, an exposure site, an exposure voltage, an exposure current, an image capture position, etc. For example, a corresponding exposure voltage or current may be selected according to the age of the object under examination; an approximate exposure location and the location of the suspension apparatus and/or wall stand apparatus, for example, the chest, leg, knee, etc., may be determined by means of the image capture site of the object under examination; the position for exposure, such as a front position, a sideways position, a back position, etc., may be acquired by means of at least one among the image capture site of the object under examination, possible disease types, or other possible information; and whether dynamic examination is required and a corresponding preset pose may be determined by means of the information of the object under examination.

In some embodiments, the X-ray imaging system or the control apparatus or the storage apparatus stores a look up table (LUT) for preset poses corresponding to dynamic examination, in which the image capture site, the number of corresponding required poses, corresponding specific poses, and the like are saved. When the protocol selection unit 210 selects a corresponding image capture protocol and when the object under examination requires dynamic examination, a corresponding pose can be selected and displayed accordingly. For example, when image capture of a lesion of a knee joint for the current object under examination is required, dynamic examination needs to be performed. By means of the look up table, three poses required for the current lesion can be acquired. In some non-limiting embodiments, it is required to acquire corresponding X-ray images when the angle between the thigh and the lower leg is 180°, 120° and 60°, and the three poses can be selected and displayed in the graphical user interface in the display, so as to prompt an operator to perform a corresponding operation.

Although the above describes corresponding poses being determined by means of the look up table during dynamic examination, it should be understood by those skilled in the art that even in a static examination, a corresponding pose may be acquired by means of a lookup table.

The term "static examination" means that only one X-ray image needs to be captured of the object under examination, at a particular location and in a particular pose, e.g., a chest radiograph examination, while the term "dynamic examination" means that X-ray images need to be captured of the object under examination in two poses or three poses or more varying poses. It does not mean that the pose is changed during exposure, but that it is necessary to additionally acquire a second or third X-ray image after the object under examination has changed to a corresponding pose.

The X-ray imaging system or the control apparatus further includes a voice apparatus mounted inside of the scan room. The voice apparatus is configured to issue voice instructions to guide the object under examination to position.

In some embodiments, a first set of voice apparatuses is mounted inside of the scan room, and a second set of voice apparatuses is mounted inside of the control room. The first set of voice apparatuses and the second set of voice apparatuses each include a microphone and a speaker, such that the scan room and the control room can communicate, and therefore an operator in the control room can direct, by means of the voice apparatuses, the object under examination to reach a specified location, get in position in a corresponding pose, etc.

In another embodiment, the voice apparatus includes a control module and a storage apparatus. The storage apparatus stores therein intelligent guiding voices for a variety of different protocols. After a corresponding protocol is selected by means of the object under examination, the intelligent guiding voice under the protocol can also be selected. The control module can be connected and paired with a camera, and can trigger and play back the intelligent guiding voice according to the real-time location of the object under examination, and can also play back different stages of speech according to the different locations of the object under examination. For example, when the camera has captured the object under examination, a first voice segment is played back to direct the object under examination to walk to the front of the wall stand; when the camera has captured that the object under examination has walked around the wall stand, a second voice segment is played back to direct the object under examination to stand in a front position, a back position or a sideways position; when the camera has captured that the object under examination has stood in a preset position, a third voice segment is played back to direct the object under examination to position into a preset pose; and when the exposure is completed, the object under examination is directed to leave the scan room.

In some embodiments, the voice apparatus may also be a display, which, for example, plays back an intelligent guiding video in the form of a video to carry out corresponding guidance, so as to guide more visually. The display may be a tube console, or may be a display that is mounted on or around the wall stand, etc.

In some embodiments, the control apparatus further includes a source control apparatus and a detector control apparatus, which can control, according to the location, height and other information of the object under examination, the X-ray source and the detector to move or rotate to a corresponding location, so as to align the exposure site of the object under examination.

In some embodiments, the preset pose includes a first pose and a second pose, and the pose determination unit 220 is capable of determining whether the pose of the object under examination satisfies the first pose and the second pose, so as to acquire X-ray images corresponding to the first pose and the second pose, respectively. Specifically, it is possible to determine, by means of connecting lines between the key points or the included angle between the connecting lines between a plurality of key points, whether the current pose of the object under examination satisfies the first pose and/or the second pose. Of course, the preset pose can also include any number of poses, depending on the number of poses required for the image capture site defined in the look up table.

The pose determination unit 220 is further configured to identify key points on the first optical image based on a deep learning network. Specifically, by training on a data set of optical images in different poses and different locations, and corresponding key points thereof, the deep learning network can be acquired. Typically, the data set used in training can be acquired in a standard pose library, or may be acquired by means of previously captured images. By means of the trained deep learning network, corresponding key points are displayed automatically on the first optical image.

Figure 3:
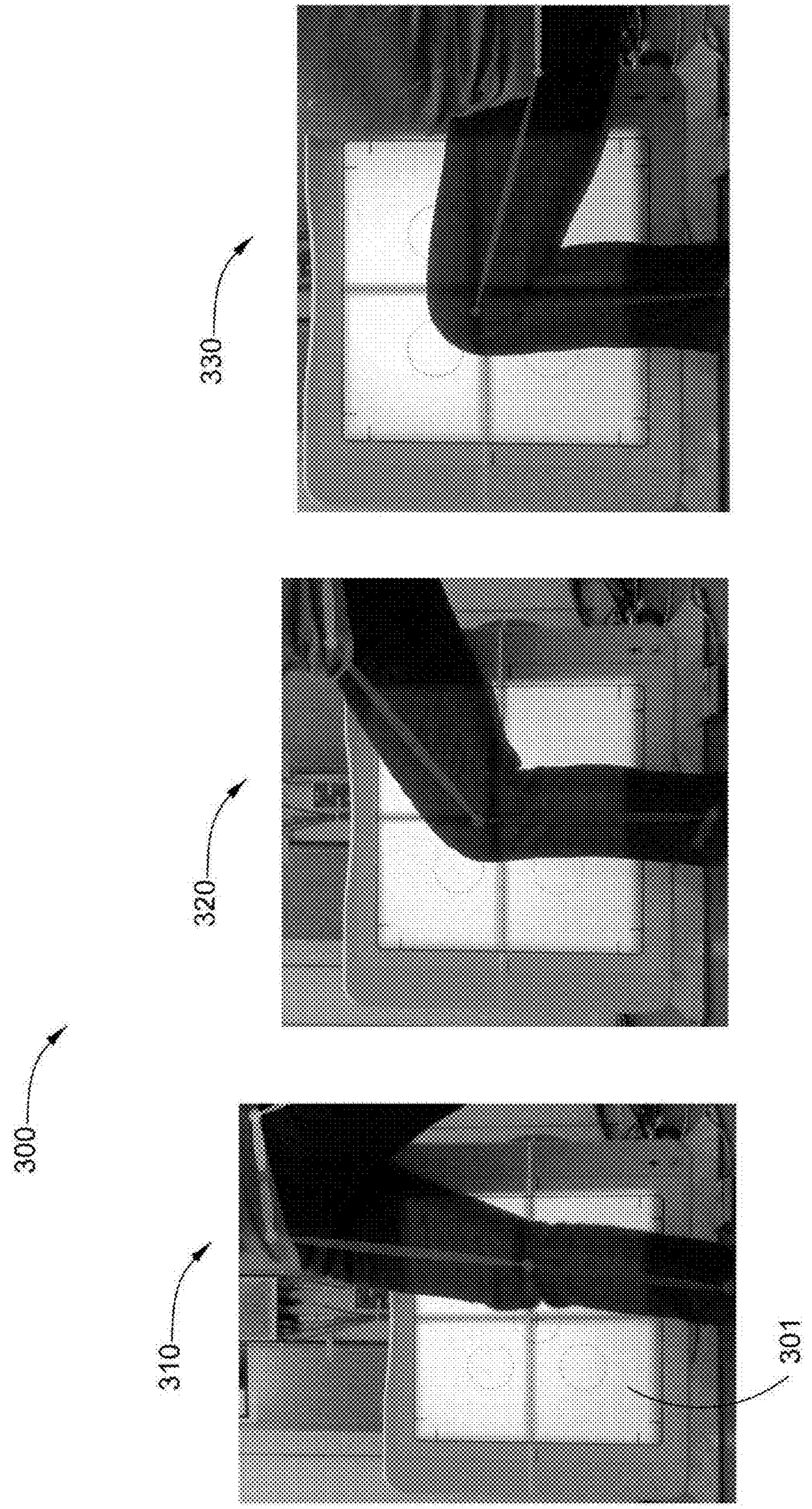
FIG. 3 is schematic diagrams of first optical images according to some embodiments of the present invention.

FIG. 3 is first optical images 300 having a preset pose according to some embodiments of the present invention. As shown in FIG. 3, in some non-limiting embodiments, for example, when the exposure site is the knee, the first optical image captures an optical image of the entire leg of the object under examination. The pose determination unit 220 can identify the location of three key points, the coccyx, the knee, and the ankle joint, on the first optical image, and can further display a connecting line between the coccyx and the knee and a connecting line between the knee and the ankle based on the protocol of three exposure poses determined by the protocol selection unit, that is, the angle between the thigh and the lower leg being 180°, 120° and 60°, and determine whether the included angle between the two connecting lines is a desired angle. Specifically, image 310 is a first optical image when the included angle between the thigh and the lower leg is 180°, image 320 is a first optical image when the included angle between the thigh and the lower leg is 120°, and image 330 is a first optical image when the included angle between the thigh and the lower leg is 60°.

Although the above shows only the location of three key points being displayed on the second optical image, it should be understood by those skilled in the art that any number of key points may be displayed, and all of the key points on the site obtained from image capturing in the current second optical image can be displayed, such as the front tip of a foot and the rear heel, and are not limited to the three key points mentioned above.

In some embodiments, the control apparatus further includes a prompt unit 260. The prompt unit 260 is capable of prompting an operator when the pose determination unit 220 determines that the current pose of the object under examination satisfies the first pose or the second pose, for example, in the form of a pop-up window in the graphical user interface, in the form of words in the graphical user interface, or in the form of a prompt tone, and the like. Specifically, when the current pose of the object under examination satisfies the first pose or the second pose, the pose determination unit 220 can generate and send a first control instruction, which can be sent to the exposure control unit 240, and of course, can also be sent to the prompt unit 260.

In general, it is required to perform image capture in the order of the poses defined in the look up table, for example, performing image capture in the order of the angle between the thigh and the lower leg being 60° to 120° to 180°. However, it should be understood by those skilled in the art that image capture may also be performed in the order of 180° to 120° to 60°. Sequentially performing image capture can acquire the state of a lesion at different poses, so as to provide more intentional aid in diagnosis. In an actual image capture process, image capture is generally performed from the most comfortable pose of the object under examination, for example, starting from an upright pose of 180°.

In some embodiments, the display of the X-ray ray imaging system includes a graphical user interface on which the first optical image can be displayed, and on the first optical image, the key points and/or connecting lines between the key points can be displayed. Furthermore, when the pose of the object under examination satisfies a preset pose, a relevant prompt can be displayed on the graphical user interface, such as by means of a pop-up window, bold text, or by displaying a different color on the first optical image, highlighting a boundary of the first optical image, and the like, so as to prompt the operator that the pose of the object under examination has satisfied the requirements of the preset pose.

In some embodiments, the location determination unit 230 can determine, based on the first optical image, whether the location of the exposure site of the object under examination is within an exposure range. As shown in FIG. 3, for example, the exposed site is the knee, the object under examination is in a sideways position at the front of the detector of the wall stand apparatus, and the camera mounted on the suspension apparatus is defined as the first camera. By means of the first optical image acquired by the first camera, the pose of the object under examination may be determined, and the exposure range or the collimation range (such as the highlighted window 301 as shown in the figure) can also be acquired. As a result, by means of the first optical image, it may be determined whether the pose of the object under examination satisfies the preset pose and whether the exposure site is within the exposure range, so as to ensure that the knee can be exposed and an X-ray image corresponding to the knee can be acquired. Preferably, the exposure site is as close as possible to an intermediate or central location of the exposure range.

In some other embodiments, the location determination unit 230 can determine, based on the second optical image, whether the location of the exposure site of the object under examination is within the exposure range. In some non-limiting embodiments, the camera mounted next to the wall stand is the first camera, and the camera mounted on the suspension apparatus is the second camera. It is necessary to determine the pose of the object under examination by means of the first optical image acquired by the first camera, otherwise the exposure range cannot be acquired on the optical image, and whether the exposure site is within the exposure range must be determined by means of the second optical image acquired by the second camera.

The exposure range refers primarily to the range of X-rays passing through the beam limiter to the detector surface, and may also be called a collimation or an exposure region. The exposure range is less than or equal to the size of the detector surface. In some non-limiting embodiments, the exposure range may be the size of the detector surface.

When the location of the exposure site is within the exposure range, the location determination unit 230 can generate and send a second control instruction, which can be sent to the exposure control unit 240, and of course, can also be sent to the prompt unit 260.

In some embodiments, the second optical image can be displayed on the graphical user interface. The exposure range is displayed on the second optical image. Optionally, the exposure range may also be displayed on the first optical image, and optionally, the profile or highlight of the exposure site may also be displayed on the first optical image or the second optical image. Furthermore, when the location of the exposure site is within the exposure range, a relevant prompt can be displayed on the graphical user interface, for example, by means of a pop-up window, bold text, or by displaying a different color on the first optical image or the second optical image, highlighting a boundary of the first optical image or the second optical image, and the like, so as to prompt the operator that the exposure site is within the exposure range.

Figure 4:
FIG. 4 is schematic diagrams of second optical images according to some embodiments of the present invention.

In some embodiments, the location determination unit 230 is further used to determine whether the distance of the image capture site of the object under examination to the detector is within a preset range. The distance of the object under examination to the detector can be acquired based on the second optical image, i.e., it is determined whether the distance between the object under examination and the detector is within the preset range. When the distance is no longer in the preset range, the object under examination may be prompted to stand close to the detector. FIG. 4 is a schematic diagram of a second optical image 400 according to some embodiments of the present invention. As shown in FIG. 4, using the knee being the capture site as an example, the second optical image 400 mounted next to the wall stand apparatus can acquire the distance of the location of the knee to the detector. When the distance exceeds the preset range, the operator or user is prompted that the object under examination is too far away from the detector, so as to avoid blurring of the acquired X-ray image.

In some non-limiting embodiments, the protocol further includes an image capture position, and the location determination unit 230 is further used to determine whether the position of the object under examination satisfies the image capture position. In some embodiments, the location determination unit 230 can further identify the position of the object under examination in an optical image. Specifically, the key points in the first optical image may be identified, and the orientation or position of the object under examination may be identified according to information of the key points. For example, when the cranium, the nasal bone, and the scapulae of the shoulders are identified, it can be determined that the object under examination is in a front position. Of course, the object under examination may also be determined to be in a left side position, a right side position, or a back position by means of a combination of information of other key points (e.g., the state or shape of connecting lines). Of course, in addition to identifying the key points, determination may be carried out by means of a deep learning network.

The exposure control unit 240 is connected to the pose determination unit 220 and the location determination unit 230, and is used to receive the first control instruction and the second control instruction, and when both the first control instruction and the second control instruction are received, control the X-ray tube to expose to acquire X-ray images corresponding to the preset poses, i.e., to acquire a first X-ray image corresponding to the first pose, and a second X-ray image corresponding to the second pose. Specifically, the exposure can be performed only if the pose of the object under examination satisfies the preset pose and the location of the exposure site is within the exposure range. When a given condition is not satisfied, then the object under examination is directed to adjust the location or pose accordingly.

Figure 5:
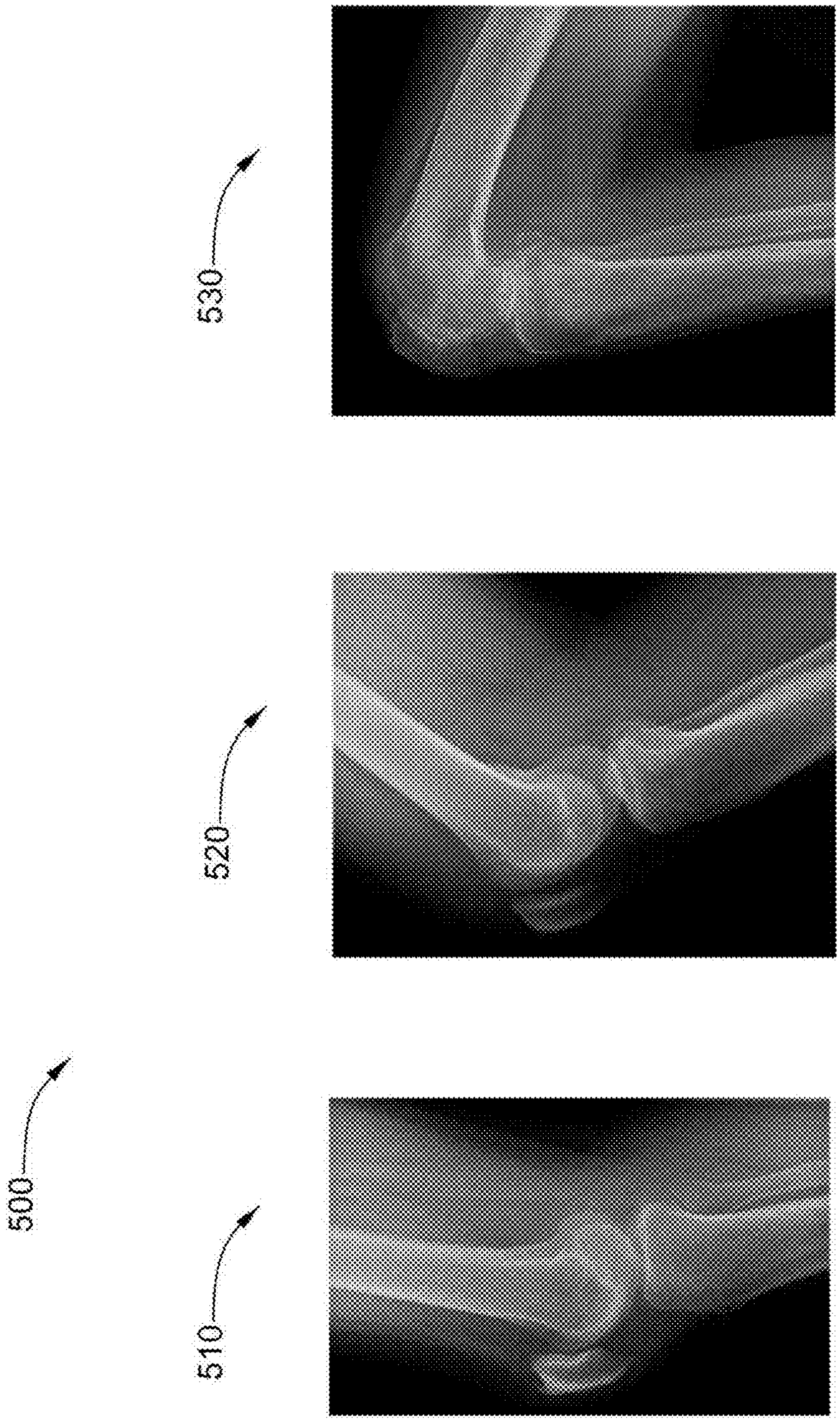
FIG. 5 is schematic diagrams of X-ray images according to some embodiments of the present invention.

The number of X-ray images corresponds to the number of preset poses corresponding to dynamic examination. FIG. 5 shows a schematic diagram of X-ray images of some embodiments of the present invention. As shown in FIGS. 3 and 5, when the number of preset poses required for dynamic examination is three, the number of acquired X-ray images is also three. By acquiring X-ray images in different poses, it is possible to assist in determining the condition of the lesion of the knee. Specifically, image 510 is an X-ray image when the included angle between the thigh and the lower leg is 180°, image 520 is an X-ray image when the included angle between the thigh and the lower leg is 120°, and image 530 is an X-ray image when the included angle between the thigh and the lower leg is 60°.

In some embodiments, a ‘ready to expose’ prompt is included on the graphical user interface. The exposure control unit 240 can control whether the prompt is displayed, that is, only when the pose of the object under examination satisfies the preset pose and the location of the exposure site is within the exposure range can the ‘ready to expose’ prompt be displayed, and the exposure can be started by means of handbrake control, so as to emit X-rays. When any one condition is not satisfied, none of the ‘ready to expose’ prompts can be displayed.

In some embodiments, when the exposure is started by means of the handbrake, an X-ray image corresponding to the first pose is first acquired; then, the object under examination is directed to change poses according to the preset second pose, during which, the handbrake has not been released, but X-rays are not emitted. When the pose of the object under examination satisfies the preset second pose and the exposure site is located within the exposure range, the control unit 240 automatically controls the tube or X-ray source to emit X-rays again, so as to acquire an X-ray image, and the handbrake is not released until all poses are captured and photographed.

In some other embodiments, when the preset first pose is satisfied and the exposure site is located within the exposure range, the handbrake is held tightly to emit X-rays to acquire the first X-ray image; then the handbrake is released, the object under examination is directed to reach the second pose, and when the second pose is satisfied and the exposure site is located within the exposure range, the ‘ready to expose’ prompt is displayed again, and then once again, the handbrake is held tightly to emit X-rays; and the process is repeated until all poses are captured.

Figure 6:
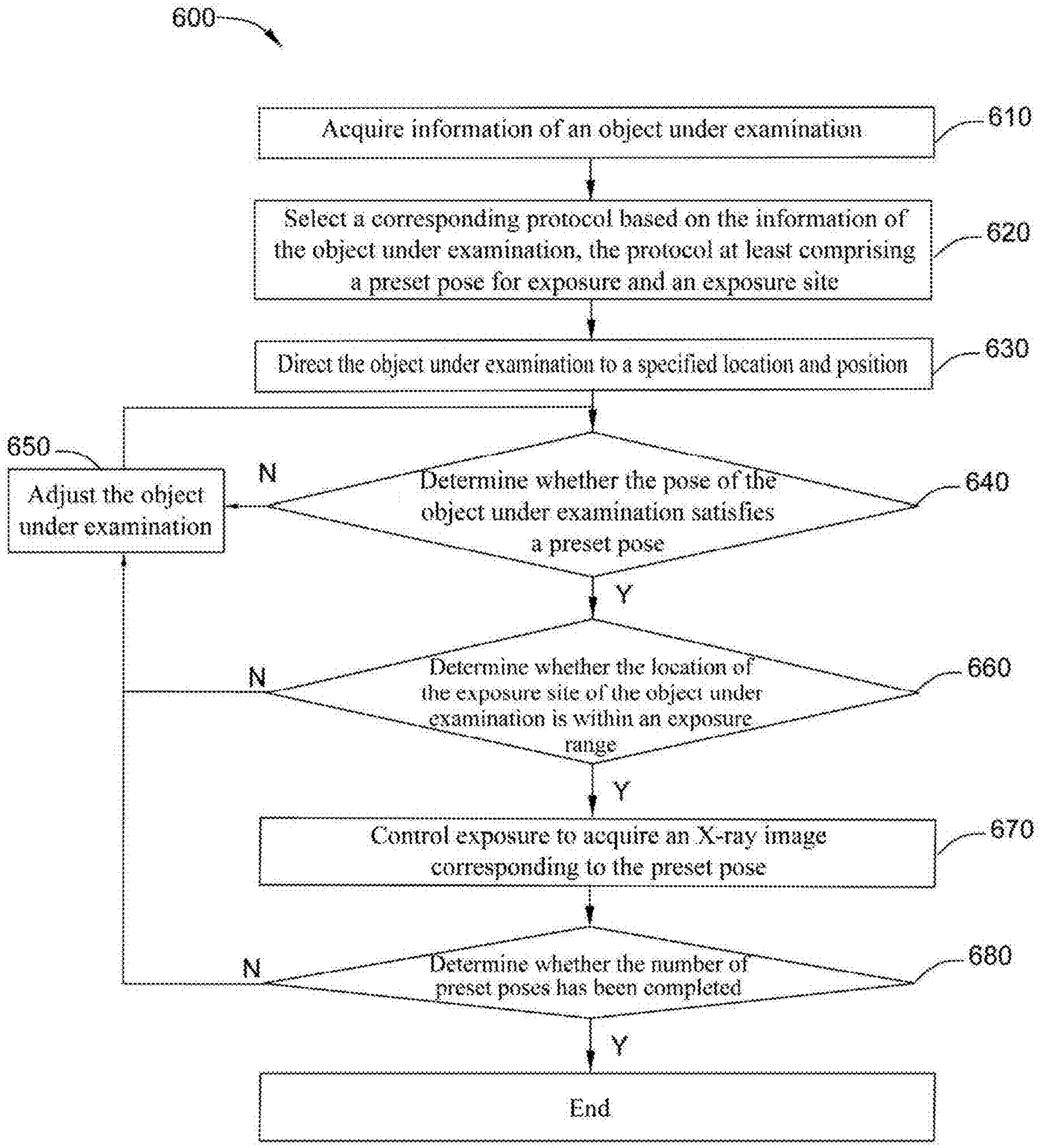
FIG. 6 is a schematic diagram for dynamic examination according to some embodiments of the present invention.

FIG. 6 is a schematic diagram of dynamic examination according to some embodiments of the present invention. As shown in FIG. 6, first, it is required to acquire information of an object under examination 610, for example, by using a first camera, a second camera, or a card reading device to scan a two-dimensional code, a barcode, an identity card, a radio frequency tag (RFID), a medical card, etc., of a patient, so as to obtain at least one among the name, age, exposure site, possible disease type, kind of image capture, and other information of the object under examination. Next, based on the information of the object under examination, a corresponding protocol is selected 620, the protocol at least comprising a preset pose for exposure and an exposure site. Specifically, at least one preset pose required for exposure is acquired according to a pre-stored look up table. Then, the object under examination is directed to a specified location and to get in position 630, for example, by using a voice apparatus (smart or from an operator) to direct the object under examination to a wall stand apparatus, and the object under examination is directed to get in position according to the preset pose, and at the same time, according to the exposure site in the protocol, an X-ray source and a detector are controlled to move or rotate to align the exposure site.

Next, it is determined whether the pose of the object under examination satisfies the preset pose 640. When the current pose does not satisfy the preset first pose, the pose of the object under examination is adjusted 650. While adjusting, it can be determined whether the current pose satisfies the first pose. When the current pose satisfies the preset first pose, it is determined whether the location of the exposure site of the object under examination is within an exposure range 660. If not within the exposure range, the location of the object under examination is adjusted 650. If within the exposure range, the X-ray source is controlled to expose and an X-ray image of the first pose is acquired 670. Thereafter, it is determined whether the number of preset poses has been completed 680. For example, when it is required in the protocol to capture two poses, the object under examination is adjusted according to the requirements of the second pose 650, and the pose 640 and the location 660 are determined repeatedly, and the X-ray image corresponding to the second pose is acquired 670, until the X-ray images corresponding to all of the required poses are acquired.

Using the knee of a patient A being the capture site as an example, first, the identity information of the patient A is acquired, then the protocol selection unit 210 can select an image capture protocol corresponding to the information, the protocol including, but not limited to, image capture poses of 180° to 120° to 60° required for dynamic examination, the capture site being the knee, the position being the front position, and the like, and then the patient A is directed to the front of the detector of the wall stand, and is positioned according to the first pose of 180°, while the X-ray source and the detector are moved, according to the information of the patient A, to align with the location of the knee of the patient A. Then, according to the acquired first optical image, it is determined whether the included angle of the connecting lines between the key points is 180°, and when 180° is reached and the knee is determined, by means of the first optical image or the second optical image, to be currently located within the exposure range, X-rays are emitted, and a first X-ray image is acquired. Next, A is directed to move to the second pose 120°, and when it is determined according to the first optical image that the pose is indeed 120° and that the knee is located within the exposure range, X-rays are emitted, and a second X-ray image is acquired. Finally, A is directed to move to the third pose 60°, and when it is determined according to the first optical image that the pose is indeed 60° and that the knee is located within the exposure range, X-rays are emitted, and a third X-ray image is acquired. Thus, the three poses and three X-ray images required for dynamic examination are completed.

During exposure, the determination of the included angle of the connecting lines between the key points by means of the second optical image does not necessarily need to be precisely 60°, 120°, and 180°. A certain error range may be set, for example, for a pose of 60°, the included angle may be between 55° and 65°, and of course, this error range may be freely set.

Figure 7:
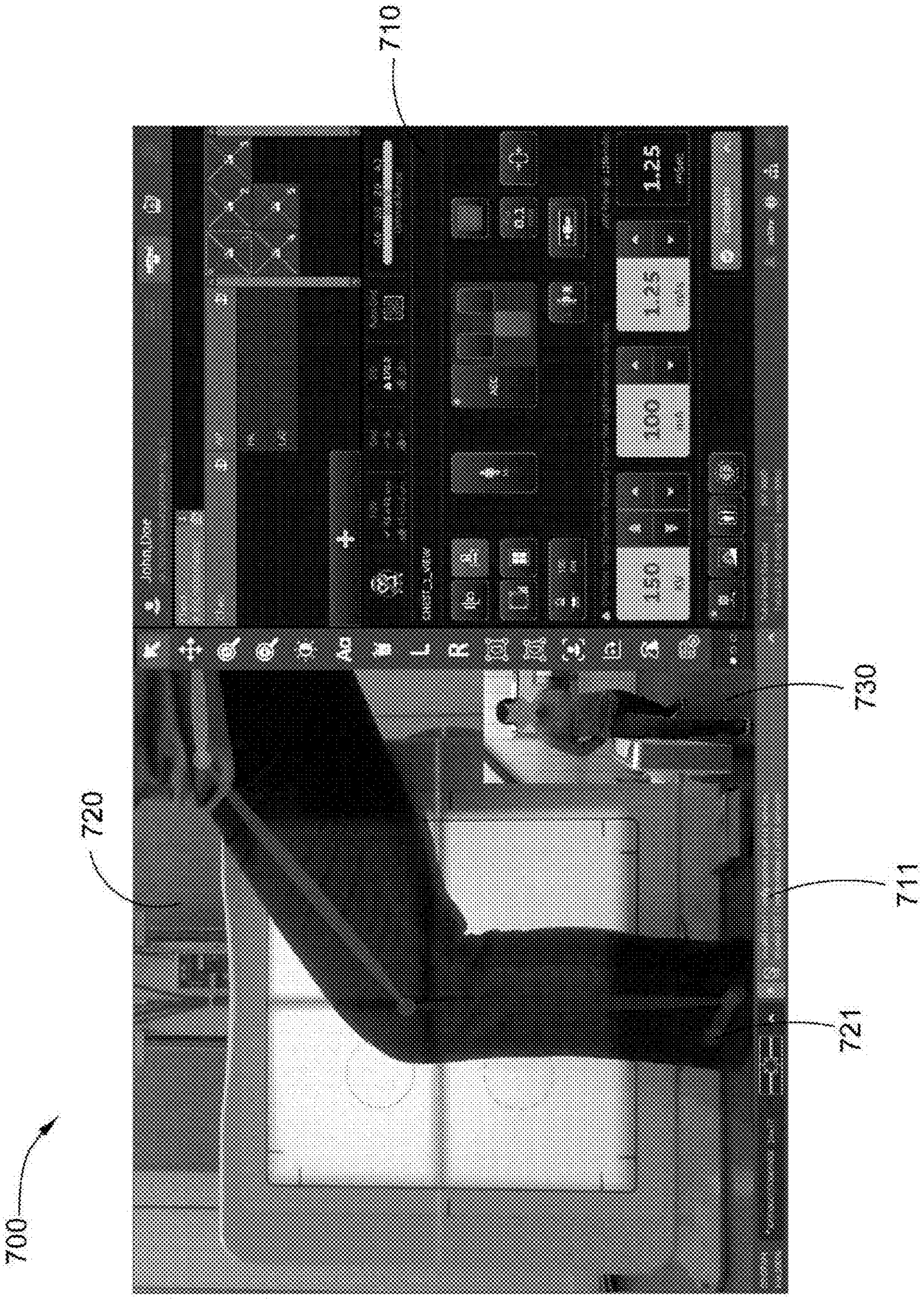
FIG. 7 is a schematic diagram of a graphical user interface according to some embodiments of the present invention.

FIG. 7 shows a schematic diagram of a graphical user interface 700 of some embodiments of the present invention. As shown in FIG. 7, the graphical user interface 700 is displayed in a display of an X-ray imaging system, for example, in a main display inside of a control room or a display of a tube controller. The graphical user interface 700 is used to display a configuration interface 710, a first optical image 720, and a second optical image 730. The configuration interface 710 includes at least one among information of an object under examination, an exposure protocol, and a 'ready to expose' prompt 711. The first optical image 720 has key points 721 and at least one among the location of an exposure site and an exposure range displayed thereon. The second optical image 730 can be used to calculate the distance from the exposure site to a detector. The 'ready to expose' prompt 711 may be displayed when the key points of the object under examination satisfy a preset pose and the location of the exposure site is within the exposure range.

In some other embodiments, the key points are displayed on the first optical image, and the at least one among the location of the exposure site and the exposure range is displayed on the second optical image.

In some embodiments, the first optical image 720 and the second optical image 730 are displayed in the left half of the graphical user interface, while the configuration interface 710 is displayed in the right half of the graphical user interface. Of course, the first optical image 720 and the second optical image 730 may also be displayed in the right half of the graphical user interface, and the configuration interface 710 displayed in the left half of the graphical user interface.

Specifically, the second optical image 730 can be displayed as a small reference box in any corner of the first optical image 720, and the second optical image can be moved, enlarged, shrunk, or deleted. Of course, the display locations of the second optical image 730 and the first optical image 720 may be interchanged by clicking or selecting, such that the second optical image is displayed enlarged, and the first optical image is displayed as the small reference box. By clicking the small reference box again, the display location of the two can be interchanged again.

Of course, the first optical image 720 and the second optical image 730 may also be displayed side by side in the graphical user interface. The means by which the first optical image 720 and the second optical image 730 are displayed are not limited.

Specifically, the configuration interface 710 may display the information of the object under examination, the exposure site, the image capture position, the exposure voltage, the exposure current, the selection of ionization chamber, the 'ready to expose' prompt, and the like. The configuration interface is not limited to the arrangement shown in FIG. 7, and there may also be any suitable configuration interface.

In some embodiments, the graphical user interface further includes a pop-up window or a prompt window for prompting that the pose of the object under examination satisfies the preset pose, the location of the exposure site of the object under examination is within the exposure range, the position of the object under examination does not satisfy the exposure position, and the like.

Figure 8:
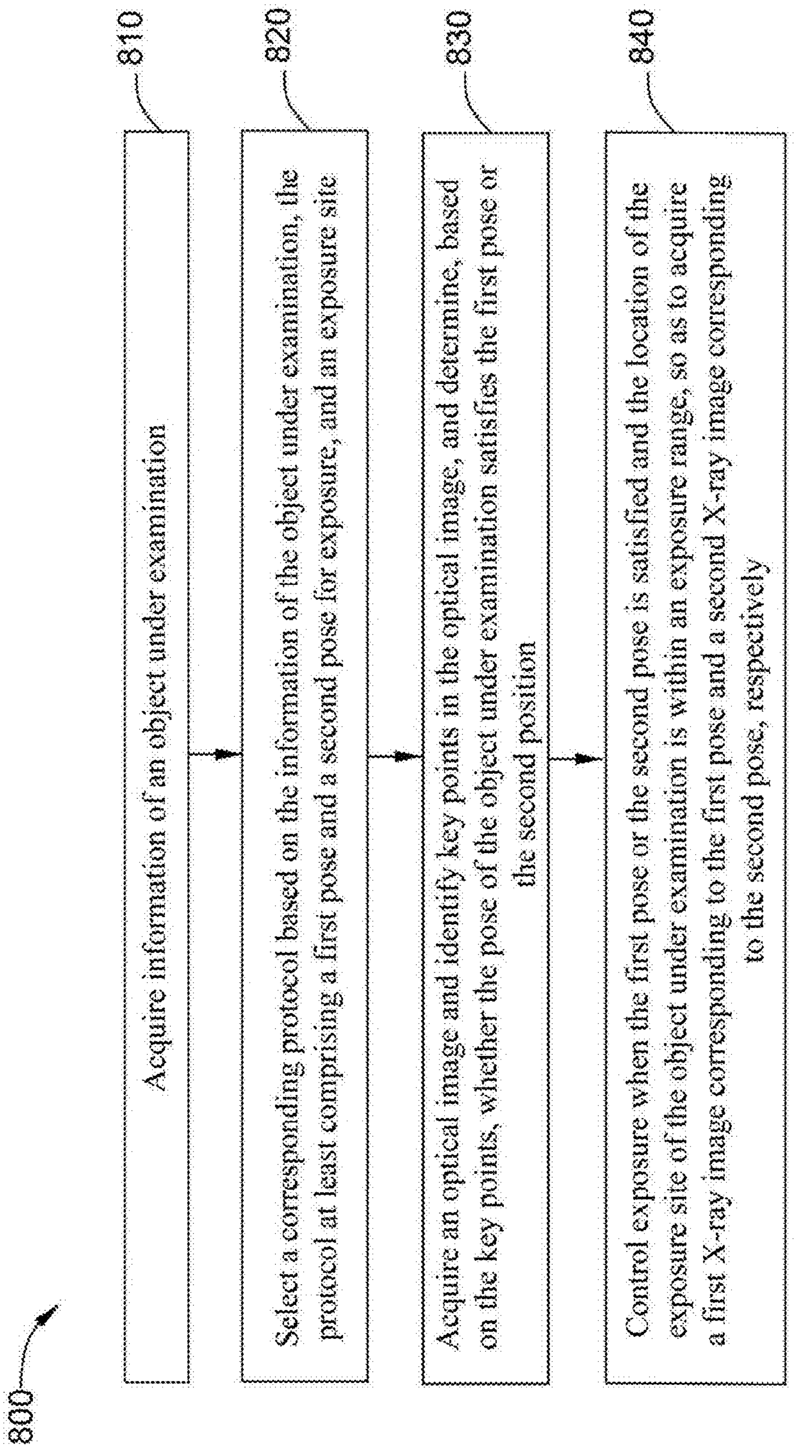
FIG. 8 is a flowchart of an X-ray imaging method for dynamic examination of some other embodiments of the present invention.

FIG. 8 shows a flowchart of an X-ray imaging method for dynamic examination of some other embodiments of the present invention. As shown in FIG. 8, the X-ray imaging method for dynamic examination 800 includes step 810, step 820, step 830, and step 840. In step 810, information of an object under examination is acquired.

Specifically, a two-dimensional code, a barcode, an identity card, a radio frequency tag (RFID), a medical card, etc. of a patient can be scanned by means of a first camera, a second camera, or a card reading device, to obtain at least one among the name, age, exposure site, possible disease type, kind of image capture, and other information of the object under examination. Of course, the information of the object under examination may also be acquired by means of medical records within the hospital or manual entry by the operator.

In step 820, based on the information of the object under examination, a corresponding protocol is selected, the protocol at least including a first pose and a second pose for exposure, and an exposure site.

Specifically, the protocol may further include an exposure voltage, an exposure current, an exposure position, etc. Of course, the protocol may further include a third pose or more poses. The number of preset poses is dependent on the number of poses required for the current dynamic examination. The number of poses and the specific poses are dependent on the exposure site and/or possible disease type, etc., of the object under examination. The information is stored in an X-ray imaging system or a control apparatus in the form of a look up table.

In step 830, an optical image is acquired and key points in the optical image are identified, and based on the key points, whether the pose of the object under examination satisfies the first pose or the second pose is determined.

Specifically, it is possible to determine whether the current pose of the object under examination satisfies the first pose and/or the second pose by means of connecting lines between the key points or an included angle between connecting lines between a plurality of key points. Of course, the preset pose can also include any number of poses, depending on the number of poses required for the image capture site defined in the look up table.

Specifically, the key points on the first optical image may be identified based on a deep learning network. By means of the trained deep learning network, corresponding key points are displayed automatically on the first optical image.

In step 840, an exposure is controlled to acquire a first X-ray image corresponding to the first pose and a second X-ray image corresponding to the second pose, respectively, when the first pose or the second pose is satisfied and the location of the exposure site of the object under examination is within an exposure range.

Figure 9:
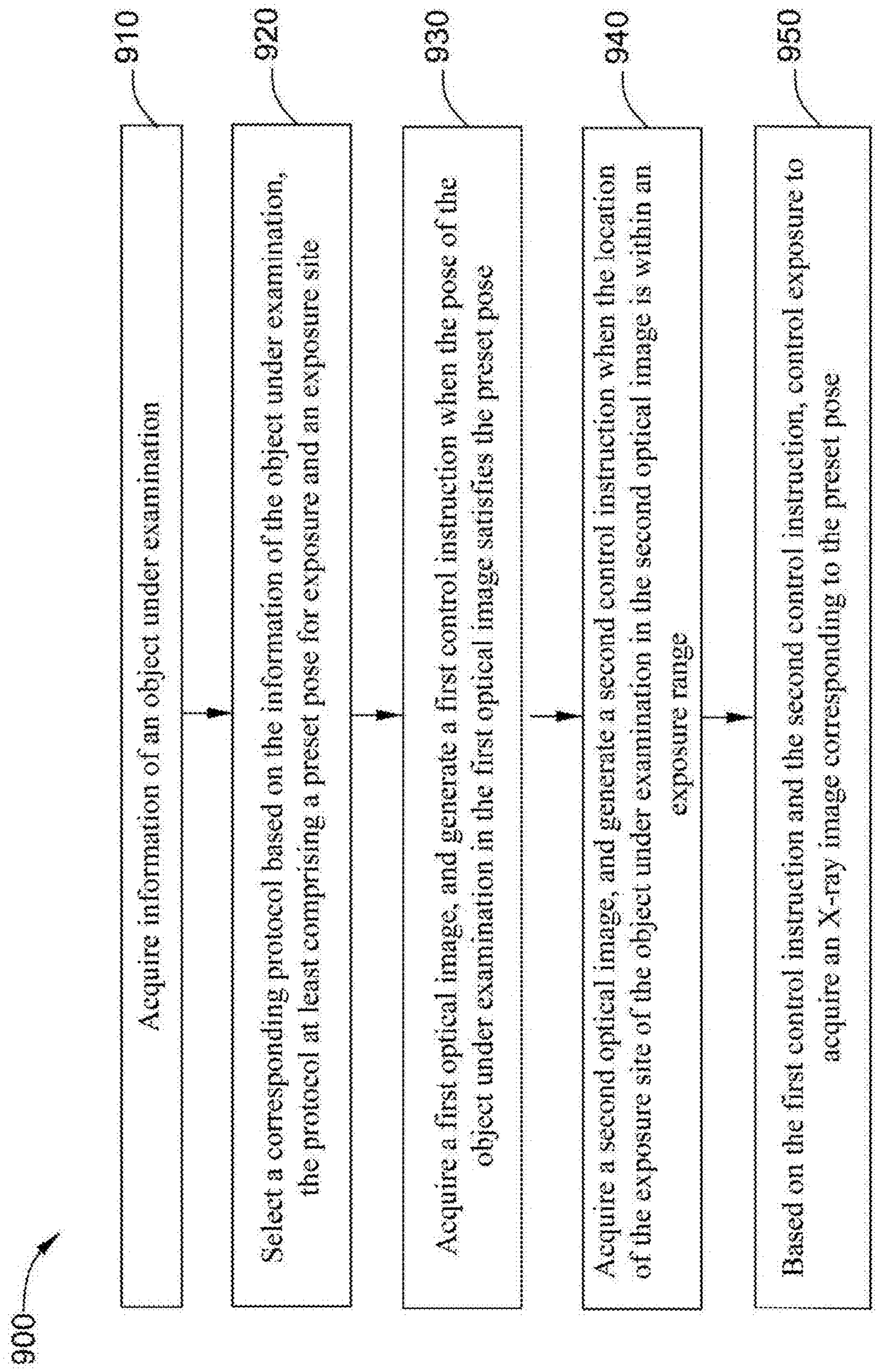
FIG. 9 is a flowchart of an X-ray imaging method for dynamic examination of some other embodiments of the present invention.

FIG. 9 shows a flowchart of an X-ray imaging method for dynamic examination of some other embodiments of the present invention. As shown in FIG. 9, the X-ray imaging method for dynamic examination 900 includes step 910, step 920, step 930, and step 940.

In step 910, information of an object under examination is acquired.

In step 920, based on the information of the object under examination, a corresponding protocol is selected, the protocol at least including a preset pose for exposure, and an exposure site.

In step 930, a first optical image is acquired, and a first control instruction is generated when the pose of the object under examination in the first optical image satisfies the preset pose.

Specifically, the first optical image is acquired by means of a first camera, and the first optical image is used to acquire the pose of the object under examination. Specifically, key points in the first optical image may be identified, e.g., by identifying the key points in the image by means of a deep learning network, and then the pose of the object under examination may be determined according to the relationship between the key points, for example, the included angle between the connecting lines or the relative position between the key points.

In step 940, a second optical image is acquired, and a second control instruction is generated when the location of the exposure site of the object under examination in the second optical image is within an exposure range.

Specifically, the second optical image is acquired by means of a second camera, and the second optical image is used to acquire the exposure range and the location of the exposure site of the object under examination. Specifically, the exposure range, i.e., a collimation region, can be displayed on the second optical image, to ensure that the exposure site is within the exposure range, and preferably, in the center of the exposure range.

In step 950, an exposure is controlled based on the first control instruction and the second control instruction to acquire an X-ray image corresponding to the preset pose.

Specifically, only when both the first control instruction and the second control instruction are received can the exposure operation be performed. When only one of the control instructions is received, the exposure operation cannot be performed, avoiding invalid exposure.

In the X-ray imaging system and the X-ray imaging method for dynamic examination of some embodiments of the present invention, first, by means disposing a camera inside of the scan room, while acquiring the pose of the object under examination, at least one among the thickness, height, location and position thereof and other information may also be obtained, and the information of the object under examination is more precise, making selection of subsequent protocols more precise. Second, in a dynamic examination scenario, by monitoring and determining by means of a front camera and a side camera, the real-time pose of the object under examination can be determined, which has guiding significance for guiding the object under examination, and also is convenient for the operator to perform corresponding operations and guidance. Third, by means of configuring exposure (or emission of X-rays) to be activated only when two conditions of the pose and the exposure range are satisfied, mis-operation by an operator can be prevented, precise exposure can be ensured, and unnecessary exposure to the object under examination due to the pose being inaccurate or exceeding the exposure range can be prevented.

Exemplary embodiments of the present invention provide an X-ray imaging system. The X-ray imaging system comprises: a first camera, used to acquire a first optical image of an object under examination; and a control apparatus, comprising: a protocol selection unit, a pose determination unit, and an exposure control unit; the protocol selection unit is used to select a corresponding protocol based on information of the object under examination, the protocol at least comprising a preset pose and an exposure site; the pose determination unit is used to identify key points on the first optical image, and determine, based on the key points, whether the pose of the object under examination satisfies the preset pose; and the exposure control unit is used to control exposure when the preset pose is satisfied and the location of the exposure site of the object under examination is within an exposure range, so as to acquire an X-ray image corresponding to the preset pose.

Specifically, the control apparatus further comprises an information acquisition unit used to acquire information of the object under examination.

Specifically, the first camera is further used to acquire the information of the object under examination.

Specifically, the information of the object under examination is acquired by scanning at least one among a barcode, a two-dimensional code, an identity card, a radio frequency tag, and a medical card of the object under examination.

Specifically, the X-ray imaging system further comprises a voice apparatus mounted inside of a scan room, configured to issue voice instructions to guide the object under examination to position.

Specifically, the preset pose comprises a first pose and a second pose, and the pose determination unit is capable of determining whether the pose of the object under examination satisfies the first pose and the second pose, so as to acquire X-ray images corresponding to the first pose and the second pose, respectively.

Specifically, the pose determination unit is further used to acquire the key points of the object under examination based on a deep learning network.

Specifically, the X-ray imaging system further comprises a second camera used to acquire a second optical image of the object under examination so as to acquire at least one among the thickness, the height, the location, and the distance to a detector surface of the object under examination.

Specifically, the X-ray imaging system further comprises a suspension apparatus and a wall stand apparatus, and one among the first camera and the second camera is mounted on the suspension apparatus, and the other among the first camera and the second camera is mounted at a side of the wall stand apparatus or inside of a scan room.

Specifically, the first camera and the second camera are perpendicularly arranged.

Specifically, the control apparatus further comprises a location determination unit used to determine, based on the first optical image or the second optical image, whether the location of the exposure site of the object under examination is within the exposure range, and the exposure control unit is capable of controlling the exposure based on control instructions outputted by the pose determination unit and the location determination unit.

Specifically, the protocol further comprises an image capture position, and the location determination unit is further used to identify the position of the object under examination in the first optical image, and determine whether the position of the object under examination satisfies the image capture position.

Specifically, the X-ray imaging system further comprises a display, used to display the first optical image and prompt information sent by the control apparatus, the prompt information comprising at least one among: the pose of the object under examination satisfying the preset pose, the location of the exposure site of the object under examination being within the exposure range, the position of the object under examination not satisfying the image capture position, and thickness information of the object under examination.

Exemplary embodiments of the present invention provide an X-ray imaging system. The X-ray imaging system comprises a processor, used to select a corresponding protocol based on information of an object under examination, the protocol at least comprising a preset pose and an exposure site; identify key points on a first optical image, and determine, based on the key points, whether the pose of the object under examination satisfies the preset pose; and control exposure when the preset pose is satisfied and the location of the exposure site of the object under examination is within an exposure range, so as to acquire an X-ray image corresponding to the preset pose.

Exemplary embodiments of the present invention provide an X-ray imaging system. The X-ray imaging system comprises a first camera, a second camera, a control apparatus, and a display; the first camera and the second camera are used to acquire a first optical image and a second optical image of an object under examination; the control apparatus is used to identify key points on the second optical image; the display comprises a graphical user interface configured to display a settings interface, the first optical image and the second optical image; the settings interface comprises at least one among information of the object under examination, an exposure protocol, and a 'ready to expose' prompt; at least one among the location of an exposure site and an exposure range are displayed on the first optical image; and the key points are displayed on the second optical image, the 'ready to expose' prompt being displayed when the key points on the second optical image satisfy a preset pose and the location of the exposure site on the first optical image is within the exposure range.

Specifically, the second optical image is displayed as a small reference box on a certain corner of the first optical image.

Specifically, the first optical image and the second optical image are interchangeable in location.

Exemplary embodiments of the present invention further provide an X-ray imaging method for dynamic examination, the method comprising: acquiring information of an object under examination; selecting a corresponding protocol based on the information of the object under examination, the protocol at least comprising a first pose and a second pose for exposure, and an exposure site; acquiring an optical image and identifying key points in the optical image, and determining, based on the key points, whether the pose of the object under examination satisfies the first pose or the second pose; and controlling exposure when the first pose or the second pose is satisfied and the location of the exposure site of the object under examination is within an exposure range, so as to acquire a first X-ray image corresponding to the first pose and a second X-ray image corresponding to the second pose, respectively.

Specifically, acquiring the information of the object under examination includes acquiring the information of the object under examination by scanning at least one among a barcode, a two-dimensional code, an identity card, a radio frequency tag, and a medical card of the object under examination.

Specifically, identifying the key points in the optical image includes acquiring the key points of the object under examination based on a deep learning network.

Specifically, the method further includes identifying the position of the object under examination, and determining whether the position of the object under examination satisfies the image capture position.

Specifically, the method further includes displaying the first optical image and prompt information sent by the control apparatus, the prompt information comprising at least one among: the pose of the object under examination satisfying the preset pose, the location of the exposure site of the object under examination being within the exposure range, the position of the object under examination not satisfying the image capture position, and thickness information of the object under examination.

Exemplary embodiments of the present invention further provide an X-ray imaging method for dynamic examination, the method comprising: acquiring information of an object under examination; selecting a corresponding protocol based on the information of the object under examination, the protocol at least comprising a preset pose for exposure and an exposure site; acquiring a first optical image, and generating a first control instruction when the pose of the object under examination in the first optical image satisfies the preset pose; acquiring a second optical image, and generating a second control instruction when the location of the exposure site of the object under examination in the second optical image is within an exposure range; and based on the first control instruction and the second control instruction, controlling exposure to acquire an X-ray image corresponding to the preset pose.

The present invention may further provide a non-transitory computer-readable storage medium for storing an instruction set and/or a computer program. When executed by a computer, the instruction set and/or computer program causes the computer to perform the image processing distribution method. The computer executing the instruction set and/or computer program may be a computer of a medical imaging system, or may be other apparatuses/modules of the medical imaging system. In one embodiment, the instruction set and/or computer program may be programmed into a processor/control apparatus of the computer.

Specifically, when executed by the computer, the instruction set and/or computer program causes the computer to: acquire information of an object under examination; select a corresponding protocol based on the information of the object under examination, the protocol at least comprising a first pose and a second pose for exposure, and an exposure site; acquire an optical image and identify key points in the optical image, and determine, based on the key points, whether the pose of the object under examination satisfies the first pose or the second pose; and control exposure when the first pose or the second pose is satisfied and the location of the exposure site of the object under examination is within an exposure range, so as to acquire a first X-ray image corresponding to the first pose and a second X-ray image corresponding to the second pose, respectively.

The instructions described above may be combined into one instruction for execution, and any of the instructions may also be split into a plurality of instructions for execution. Moreover, the present invention is not limited to the instruction execution order described above.

As used herein, the term "computer" may include any processor-based or microprocessor-based system, including a system using a microcontrol apparatus, a reduced instruction set computer (RISC), an application-specific integrated circuit (ASIC), a logic circuit, and any other circuit or processor capable of performing the functions described herein. The examples above are exemplary only and are not intended to limit the definition and/or meaning of the term "computer" in any way.

The instruction set may include various commands used to instruct the computer serving as a processing machine or the processor to perform specific operations, for example, methods and processes of various embodiments. The instruction set may be in the form of a software program that may form part of one or more tangible, non-transitory computer readable media. The software may be in various forms of, for example, system software or application software. Furthermore, the software may be in the form of a standalone program or a collection of modules, a program module within a larger program, or part of a program module. The software may also include modular programming in the form of object-oriented programming. Processing of input data by the processing machine may be in response to an operator command, or in response to a previous processing result, or in response to a request made by another processing machine.

As used herein, the term "computer" may include any processor-based or microprocessor-based system, including a system using a microcontrol apparatus, a reduced instruction set computer (RISC), an application-specific integrated circuit (ASIC), a logic circuit, and any other circuit or processor capable of performing the functions described herein. The examples above are exemplary only and are not intended to limit the definition and/or meaning of the term "computer" in any way.

Some exemplary embodiments have been described above; however, it should be understood that various modifications may be made. For example, suitable results can be achieved if the described techniques are performed in a different order and/or if components in the described systems, architectures, devices, or circuits are combined in different ways and/or replaced or supplemented by additional components or equivalents thereof. Accordingly, other implementations also fall within the scope of protection of the claims.

The invention claimed is:

1. An X-ray imaging system, comprising:

a first camera, configured to acquire a first optical image of an object under examination; and a control apparatus, comprising:

a protocol selection unit, configured to select a corresponding protocol based on information of the object under examination, the protocol at least comprising a preset pose and an exposure site;

a pose determination unit, configured to identify key points on the first optical image, and determine, based on the key points, whether the pose of the object under examination satisfies the preset pose; and an exposure control unit, configured to control exposure when the preset pose is satisfied and the location of the exposure site of the object under examination is within an exposure range, so as to acquire an X-ray image corresponding to the preset pose, wherein the X-ray imaging system further comprises a second camera configured to acquire a second optical image of the object under examination, so as to acquire at least one among the thickness, the height, the location, and the distance to a detector surface of the object under examination.

2. The X-ray imaging system according to claim 1, wherein the control apparatus further comprises an information acquisition unit configured to acquire information of the object under examination.

3. The X-ray imaging system according to claim 2, wherein the information of the object under examination is acquired by scanning at least one among a barcode, a two-dimensional code, an identity card, a radio frequency tag, and a medical card of the object under examination.

4. The X-ray imaging system according to claim 1, wherein the first camera is further configured to acquire information of the object under examination.

5. The X-ray imaging system according to claim 1, wherein the system further comprises: a voice apparatus mounted inside of a scan room, the voice apparatus being configured to issue voice instructions to guide positioning of the object under examination.

6. The X-ray imaging system according to claim 1, wherein the preset pose comprises a first pose and a second pose, and the pose determination unit is capable of determining whether the pose of the object under examination satisfies the first pose and the second pose, so as to acquire X-ray images corresponding to the first pose and the second pose.

7. The X-ray imaging system according to claim 1, wherein the pose determination unit is further configured to acquire the key points of the object under examination based on a deep learning network.

8. The X-ray imaging system according to claim 1, wherein the X-ray imaging system comprises a suspension apparatus and a wall stand apparatus, one among the first camera and the second camera being mounted on the suspension apparatus, and the other among the first camera and the second camera being mounted at a side of the wall stand apparatus or inside of a scan room.

9. The X-ray imaging system according to claim 1, wherein the first camera and the second camera are perpendicularly arranged.

10. The X-ray imaging system according to claim 1, wherein the control apparatus further comprises a location determination unit configured to determine, based on the first optical image or the second optical image, whether the location of the exposure site of the object under examination is within the exposure range, and the exposure control unit is capable of controlling the exposure based on control instructions output by the pose determination unit and the location determination unit.

11. The X-ray imaging system according to claim 10, wherein the protocol further comprises an image capture position, and the location determination unit is further configured to identify the position of the object under examination in the first optical image, and determine whether the position of the object under examination satisfies the image capture position.

12. The X-ray imaging system according to claim 1, wherein the system further comprises: a display configured to display the first optical image and prompt information sent by the control apparatus, the prompt information comprising at least one among: the pose of the object under examination satisfying the preset pose, the location of the exposure site of the object under examination being within the exposure range, the position of the object under examination not satisfying the image capture position, and thickness information of the object under examination.

13. An X-ray imaging system, comprising:

a first camera and a second camera, configured to acquire a first optical image and a second optical image of an object under examination, respectively;

a control apparatus, configured to identify key points on the first optical image; and a display, comprising a graphical user interface, the graphical user interface being configured to display a configuration interface, the first optical image, and the second optical image, the configuration interface comprising at least one among information of the object under examination, an exposure protocol, and a 'ready to expose' prompt, the key points being displayed on the first optical image, and at least one among the location of an exposure site and an exposure range being displayed on the second optical image;

wherein the 'ready to expose' prompt is displayed when the key points of the object under examination satisfy a preset pose and the location of the exposure site is within the exposure range.

* * * * *